United States Patent [19]

Leber

[11] 4,025,331
[45] May 24, 1977

[54] N-[O-(β-CYANOETHYL)-PHOSPHONOMETHYL]-GLYCINES AND DERIVATIVES

[75] Inventor: Jean-Pierre Leber, Basel, Switzerland

[73] Assignee: Sandoz Ltd., Basel, Switzerland

[22] Filed: Oct. 28, 1975

[21] Appl. No.: 625,818

[30] Foreign Application Priority Data

Nov. 1, 1974 Switzerland ............... 14673/74

[52] U.S. Cl. ............................ 71/86; 260/923; 260/924; 260/940

[51] Int. Cl.$^2$ ............ A01N 9/36; C07F 9/40

[58] Field of Search ............. 260/924, 940, 923; 71/86

[56] References Cited

UNITED STATES PATENTS

| | | | |
|---|---|---|---|
| 3,556,762 | 1/1971 | Hamm | 71/86 |
| 3,799,758 | 3/1974 | Franz | 71/86 |
| 3,929,450 | 12/1975 | Hamm et al. | 71/86 |

Primary Examiner—Richard L. Raymond
Attorney, Agent, or Firm—Gerald D. Sharkin; Richard E. Vila

[57] ABSTRACT

The present invention concerns novel phosphonomethyl glycine derivatives of the formula

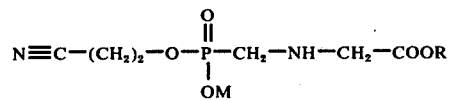

wherein
R is hydrogen, unsubstituted or substituted hydrocarbon or a cation and
M is hydrogen or a cation, possessing herbicidal and plant growth regulating properties.

17 Claims, No Drawings

N-[O-(β-CYANOETHYL)-PHOSPHONOMETHYL]-GLYCINES AND DERIVATIVES

The present invention relates to phosphonomethyl glycine derivatives possessing herbicidal and plant growth regulating properties.

Accordingly, the present invention provides compounds of formula I,

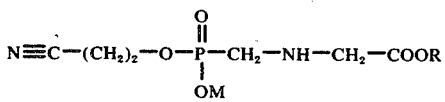

wherein
R is hydrogen, a hydrocarbon ($C_1$–$C_{12}$) unsubstituted or substituted by halogen, alkoxy ($C_1$–$C_8$), di-alkyl($C_1$–$C_8$) amino or cyano, or an agriculturally acceptable cation and M is hydrogen or an agriculturally acceptable cation.

By agriculturally acceptable cation is meant those cations which would not render the compounds unsuitable for agricultural use, e.g., those cations which are not unacceptably unstable or toxic to mammals.

When R is a substituted or unsubstituted hydrocarbon, this is preferably alkyl ($C_1$–$C_8$) unsubstituted or substituted by halogen, alkoxy ($C_1$–$C_8$) di-alkyl ($C_1$–$C_8$) amino or cyano; alkenyl ($C_2$–$C_8$) or alkynyl ($C_2$–$C_8$) unsubstituted or substituted by halogen; cycloalkyl ($C_3$–$C_8$); aryl ($C_6$–$C_{10}$) aralkyl ($C_7$–$C_{12}$); or alkaryl ($C_7$–$C_{12}$). When R is an unsubstituted or substituted hydrocarbon, this is more preferably alkyl ($C_1$–$C_8$), particularly unsubstituted alkyl ($C_1$–$C_5$). R, as a substituted hydrocarbon, is preferably mono-substituted. When R is or contains aryl, this is preferably phenyl or naphthyl, especially phenyl. When R is aralkyl, preferably this contains a $C_1$–$C_6$ alkyl or alkylene portion, especially a $C_1$–$C_2$ alkyl or alkylene portion.

When R and/or M is an agriculturally acceptable cation, this is preferably an alkali metal, an alkaline earth metal, an ammonium (including heterocyclic ammonium) or a hyrazine cation, especially an alkali metal, an alkaline earth metal or an ammonium cation of formula (a)

wherein
$R_1$, $R_2$ and $R_3$ are, independently, hydrogen or a hydrocarbon ($C_1$–$C_{20}$) unsubstituted or substituted by a group $-NR_4R_5$, wherein $R_4$ and $R_5$ are, independently, alkyl ($C_1$–$C_{20}$), a group $OR_6$,
wherein $R_6$ is hydrogen, alkyl ($C_1$–$C_{10}$) or phenyl,
or halogen, particularly sodium, potassium, or an ammonium cation of formula b

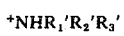

wherein
$R_1'$, $R_2'$ and $R_3'$ are each, independently, hydrogen or alkyl ($C_1$–$C_4$).

The preferred compounds of formula I are accordingly the compounds of formula Ia,

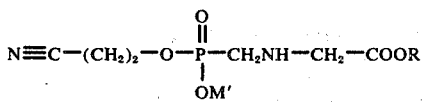

wherein
R' is hydrogen, alkyl ($C_1$–$C_5$) or a sodium or potassium cation or a cation of formula (b) above, and
M is hydrogen, a sodium or potassium cation or a cation of formula b above.

By the term "halogen" as employed herein is meant fluorine, chlorine, bromine and iodine, preferably bromine and chlorine, especially chlorine.

When either of R or M is, or as the case may be, includes, a hydrocarbon group, e.g., alkyl, then this may be straight or branched chain, primary, secondary or tertiary. Preferably such hydrocarbon groups are alkyl, especially alkyl ($C_1$–$C_5$), more especially alkyl ($C_1$–$C_4$) e.g., methyl or ethyl.

When M is hydrogen, then as will be appreciated, tautomerism is possible by way of the formation of an internal salt.

The compounds of formula I may be produced in accordance with a further aspect of the present invention by hydrolyzing a compound of formula II,

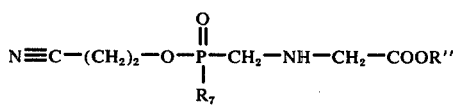

wherein
R'' has one of the unsubstituted or substituted hydrocarbon significances of R and
$R_7$ is a radical

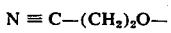

or a radical -OM
wherein M is as defined above,
and when the resulting product is a carboxylic acid, when required, converting the resulting product into agriculturally acceptable salt form.

As will be appreciated, when $R_7$ is a β-cyanoethoxy radical, then the hydrolysis may comprise only partial hydrolysis, namely hydrolytic splitting off of β-cyanoethanol or β-cyanoethoxide or its further decomposition products, or full hydrolysis, namely with additional saponification of the carboxylic ester moiety.

The hydrolysis is preferably effected by heating, e.g., to between 80° and 100° C, preferably under reflux, with water. An organic solvent such as acetone, acetonitrile, dioxane, or dimethylformamide may also be employed, although the reaction is preferably effected in the absence of such a solvent. The degree of hydrolysis will naturally vary depending on the amount of water and the reaction time, e.g., equimolar amount and 1 to 2 hours for partial hydrolysis, and 50 to 200-fold molar excess of water and 12 to 20 hours for saponification of the carboxylic ester group.

The free carboxylic acid may be converted to agriculturally acceptable salt form and vice versa in manner known per se.

The compounds of formula II wherein $R_7$ is a β-cyano-ethoxy group may be obtained by condensing the compound of formula III $(N≡C-CH_2-CH_2-O)_2-P-OH$     III with a compound of formula IV $H_2C=N-CH_2-COOR'$     IV wherein R' is as defined above (believed to exist in the form of a trimer).

The reaction, which is initially exothermic, is preferably effected in the absence of a solvent at a temperature of e.g., 80° to 120° C.

The compounds of formula IV are produced in conventional manner by condensing a compound of formula VI, $HCl . H_2N-CH_2-COOR'$     VI wherein R' is as defined above, with aqueous formaldehyde in the presence of a base such as sodium hydroxide.

The compounds of formula I exhibit herbicidal properties against representative monocotyledonous weeds such as Alopecurus myosuroides, Echinochloa crus galli, Avena fatua, Agropyron repens and Cyperus rotundus, and representative dicotyledonous weeds such as Amaranthus retroflexus, Anthemis spec., Capsella bursa pastoris, Centaurea cyanus, Chenopodium album, Cirsium arvense, Convolvulus arvensis, Convolvulvus sepium, Galeopsis spec., Galium aparine, Lamium spec., Matricaria spec. Plantago spec., Polygonum spec., Ranunculus arvensis, Raphanus raphanistrum, Senecio vulgaris, Sinapis arvensis Stellaria media, Veronica spec., Vicia spec., Viola tricolor, and Thlaspi arvense when applied pre-and post-emergence at a dosage of 5 kg/hectare. The compounds in particularly exhibit a herbicidal effect against representative perennial weeds such as Cyperus rotundus, Convolvulvus sepium, Agropyron repens and Sorphum halepense as indicated by the inhibition of shooting in the plant rhizomes up to 60 days after the application of 5 kg/hectare of the compounds to the plants at the 2 – 3 leaf stage thereof and the pruning off of the dead plant parts above ground. On the other hand, the compounds exhibit a substantially lower to negligible herbicidal effect in the cultivated plants cotton, sugar been, potato, alfalfa and maize at 5 kg/hectare pre- and post-emergence of the plants.

Accordingly, the compounds of formula I are indicated for use as herbicides, particularly in the combating of perennial weeds or the selective combating of weeds in cultivated crops such as cotton, sugar beet, potato, alfalfa and maize.

The compounds of formula I also exhibit plant growth regulating effects in cultivated crops such as cucumber and beans as indicated in Tests 1 and 2 below.

TEST 1:

Determination of the germination rate, shoot and root growth (cell division) in cucumbers (Cucumis sativus L)

Cucumber seeds are placed on a Nybold net of suitable mesh size. THe net is in contact with the surface of a Knop nutrient solution in a plastic beaker containing the active substances to be tested at dosages of 125 ppm. 16 Seeds are used per beaker. The germination rate is determined, and the growth in length of the shoots and roots is measured, and other growth effects are visually determined after 7 days in comparison to untreated control plants.

| Active substance of general formula I | Germination in % | Shoot length % (Untreated control plants = 100%) | Root length in % | Other effects |
|---|---|---|---|---|
| Sodium salt of the N-[0-(β-cyanoethyl)-phosphonomethyl]-aminoacetic acid ethyl ester dihydrate | 107 | 43 | 43 | shoot GI |
| Dimethylammonium salt of the N-[0-(β-cyanoethyl)-phosphonomethyl]-amino-acetic acid ethyl ester dihydrate | 100 | 40 | 10 | shoot GIBZR root BA |
| Isopropyl ammonium salt of the N-[0-(β-cyanoethyl)-phosphonomethyl]-amino-acetic acid ethyl ester hemihydrate | 95 | 30 | 5 | shoot GIDZR root B |

The abbreviations used under "other effects" have the following meanings:
GI = Growth inhibition of the leaves
A = Auxin effect, curvatures, thickening of the whole plant
D = Increase of colour intensity in the whole plant
B = Burning
R = Rooting
H = Inhibition of the lateral root formation
Z = Destruction of the apical meristem

TEST 2

Defoliation (plant section method) in bean plants (Phaseolus vulgaris)

Plant sections are prepared of 3 to 4 week old bean plants, consisting of the 1 cm long petioli sections of the primary leafs and the 3 cm long epicotyle segment and containing abscissa zones.

Five plant sections each are inserted into moist inert artificial moss pieces (3.5 × 3.5 × 1.2 cm). The cut surfaces of the petioli are immersed approximately 0.5 cm deep into the test solutions containing the active substances of general formula I at a dose of 500 ppm, for 1 minute. Subsequently the plant section units are placed into petri dishes, covered with a plastic container and kept in the dark at 25° C. The number of petioli which fall off is determined and is compared with those of untreated control plants.

| Active substance | % Petioli fallen off compared with control 4 days after application |
|---|---|
| Dimethylammonium salt of the N-[o-(β-cyanoethyl)-phosphonomethyl]-aminoacetic acid ethyl ester dihydrate | 60 |
| Isopropylammonium salt of the N-[O-(β-cyanoethyl)-phosphonomethyl]-aminoacetic acid ethyl ester dihydrate | 90 |

Untreated plants = 0%

The compounds are therefore furthermore indicated for use as plant growth regulators, primarily for the initiation or acceleration of the so-called physiological maturing or ageing processes in cultivated plants. Such physiological processes include budding, fruit and seed formation, tuber and root formation and generally those processes technically referred to as "abscissions," e.g., defoliation and fruit fall. Initiation or acceleration of the physiological maturing or ageing processes is of particular interest in fruit crops such as citrus, pineapple and tomato and in tobacco, hemp and cotton.

For the above-mentioned uses, the amount of compound applied to a locus containing the weed and/or crop will naturally vary, depending, for example, on the desired effect, the type and age of plant, time of application and climatic conditions. However, in general, satisfactory results are obtained when applied to a locus at a dosage of from 1 to 10 kg/hectare in the case of herbicide use, preferably 3.5 to 8 kg/hectare, especially 4 to 5 kg/hectare, and 1 to 5 kg/hectare in the case of plant growth regulator use, preferably 2 to 3 kg/hectare.

For the above-mentioned uses, the compounds may be employed in association with herbicide or plant growth regulator carriers, diluents and adjuvants (e.g., surfactants) in the form of herbicidal or plant growth regulator compositions, respectively. Such carriers, diluents and adjuvants are conventional. Examples of compositions are as follows, viz.

Wettable powder

25 Parts by weight of the sodium salt of N-[O-(β-cyanoethyl)-phosphonomethyl]-aminoacetic acid ethyl ester, 5 parts by weight of a condensation product consisting of formaldehyde and naphthalene sulphonate, 2 parts by weight of alkylphenyl sulphonate, 5 parts by weight of dextrine, 1 part by weight of ammonium caseinate and 62 parts by weight of diatomaceous earth are mixed homogeneously and subsequently ground to an average particle size of considerably below 45 microns. The resulting powder may be employed for herbicidal use.

Emulsion concentrate

10 Parts by weight of isopropylammonium salt of N-[O-(β-cyanoethyl)-phosphonomethyl]-aminoacetic acid ethyl ester hemihydrate are mixed with 10 parts by weight of a non-ionic emulsifier (iso-octylphenylpolyglycol ether) and 80 parts by weight of water. The emulsion concentrate may be diluted with water to the desired concentration. Said diluted form may be employed for herbicide and plant growth regulator use.

The following Examples illustrate the production of the compounds of formula I. Temperatures are in ° centigrade and parts and percentages are by weight.

EXAMPLE 1

N-[O-(β-cyanoethyl)-phosphonomethyl]-glycine

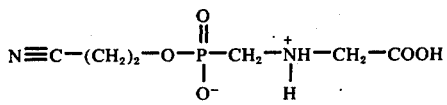

25 g (0.1 mols) of ethyl N-[O-(β-cyanoethyl)-phosphonomethyl]-aminoacetate in 200 ml of water are heated under reflux for 16 hours. The water is then evaporated off in vacuo in a rotary evaporator and the residue is dried at 50° under high vacuum. Thereafter the residue is warmed with 300 ml of ethanol.

Recrystallization of the crude product from 50 ml of water affords a pure product m.p. 214° – 215°.

Analysis: C$_6$H$_{11}$N$_2$O$_5$P Molecular weight: 222.14

Calc.: C, 32.4%; H, 5.0%; N, 12.6%; P, 11.8%;
Found: C, 32.0%; H, 5.2%; N, 12.3%; P. 13.3%.

EXAMPLE 2

Sodium salt of N-[O-(β-cyanoethyl)-phosphonomethyl]-glycine hydrate

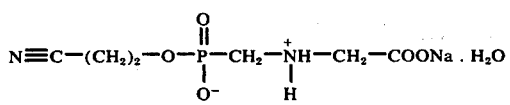

To a solution of 4.44 g (0.02 mol) of N-[O-(β-cyanoethyl)-phosphonomethyl]-glycine in 100 ml of water are added 20 ml (0.02 mol) of 1N sodium hydroxide solution with stirring. Afer the mixture has been heated for a short time, the water is evaporated off in vacuo in a rotary evaporator at 50°, yielding a product in the form of crystals m.p. 101°.

Analysis: C$_6$H$_{10}$N$_2$O$_5$PNa.H$_2$O Molecular weight: 262.13

Calc.: C, 27.5%; H, 4.6%; N, 10.7%; P, 11.8%;
Found: C, 27.9%; H, 4.5%; N, 10.7%

By heating the hydrate product for a period of 2 hours under high vacuum at 50° the corresponding anhydrous product, m.p. 146°, can be obtained.

Analysis: C$_6$H$_{10}$N$_2$O$_5$PNa Molecular weight: 244.12

Calc.: C, 29.5%; H, 4.1%; N, 11.5%; P, 12.7%;
Found: C, 29.5%; H, 4.7%; N, 11.5% P, 12.0%.

EXAMPLE 3

Mono-isopropylammonium salt of N-[O-(β-cyanoethyl)-phosphonomethyl]-glycine hydrate

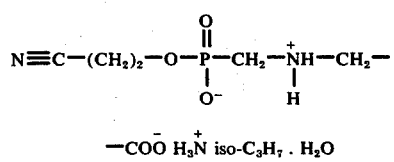

This compound is produced in an analogous manner to that described in Example 2, using isopropylamine instead of sodium hydroxide. Its melting point is 156 – 158°.

Analysis: $C_9H_{20}N_3O_5P \cdot H_2O$ Molecular weight: 299.26

Calc.: C, 36.1%; H, 7.4%; N, 14.0%; P, 10.35%; Found: C, 35.9%; H, 7.2%; N, 14.2%; P, 9.9%.

By heating the hydrate product for a period of 2 hours under high vacuum at 50° the corresponding anhydrous product, m.p. 163°, can be obtained.

Analysis: $C_9H_{20}N_3O_5P$ molecular weight: 231.25

Calc.: C, 38.4%; H, 7.2%; N, 14.9% P, 11.0%; Found: C, 38.5%; H, 7.3%; N, 15.0%; P, 10.8%.

EXAMPLE 4

Dimethylammonium salt of
N-[O-(β-cyanoethyl)-phosphonomethyl]-glycine dihydrate

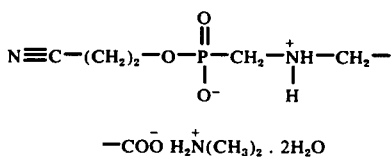

In an analogous manner to those described in Examples 2 and 3, the title compound is produced as a resinous material. NMR(δ,ppm) in $D_2O$ protons of —$CH_2$ adjacent to the P atom appear as a doublet at 3.32; those of —$CH_2$ adjacent to the carboxylate group appear as a singlet at 3.75.

By heating the hydrate product at 50° under high vacuum for 2 hours the corresponding anhydrous product is obtained having a glassy appearance.

Analysis: $C_8H_{18}N_3O_5P$ Molecular weight: 267.22

Calc.: C, 36.0%; H, 6.8%; N, 15.7%; P, 11.6%; Found: C, 35.7%; N, 6.9%; N, 15.5%; P, 11.2%.

EXAMPLE 5

Disodium salt of
N-[O-(β-cyanoethyl)-phosphonomethyl]-glycine hydrate

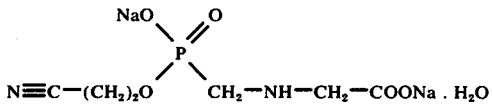

To a solution of 4.44 g (0.02 mol) of N]O-(β-cyanoethyl)-phosphono]-methylglycine in 100 ml of water are added 40 ml (0.04 mol) of 1N sodium hydroxide solution with stirring. After evaporation of the water at 50° in a rotary evaporator under reduced pressure from a water pump the product is obtained as crystals, m.p. 127°.

Analysis: $C_6H_9N_2O_5PNa_2 \cdot H_2O$ Molecular weight:284.12

Calc.: C, 25.4%; H, 3.9%; N, 9.9%; P, 10.9%; Found: C, 25.6%; H, 4.1%; N, 9.8%; P, 9.9%.

By heating the hydrate product at 50° under high vacuum for 2 hours the corresponding anhydrous product is obtained as crystals with m.p. 220° (with decomposition).

Analysis: $C_6H_9N_2O_5PNa_2$ Molecular weight: 266.10

Calc.: C, 27.1%; H, 3.4%; N, 10.5%; P, 11.6%; Found: C, 26.8% H, 3.6%; N, 10.6%; P, 11.2%.

EXAMPLE 6

Di-isopropylammonium salt of
N-[O-(β-cyanoethyl)-phosphonomethyl]-glycine hydrate

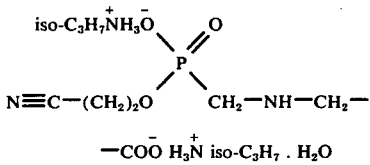

This compound in non-crystalline form is produced in an analogous manner to that described in Example 5.

Analysis: $C_{12}H_{29}N_4O_5P \cdot H_2O$ Molecular weight: 358.38

Calc.: C, 40.2%; H, 8.7%; N, 15.6%; P, 8.6%; Found: C, 39.2%; H, 9.2%; N, 15.2%; P, 8.8%;

NMR (δ, ppm) in $D_2O$: protons of —$CH_2$— adjacent to the P atom appear as a doublet at 3.17; those of —$CH_2$— adjacent to the carboxylate group appear as a singlet at 3.59.

By heating the hydrated product at 50° under high vacuum for 2 hours, the corresponding anhydrous product, m.p. 128°, is obtained.

Analysis: $C_{12}H_{29}N_4O_5P$ Molecular weight: 340.36

Calc: C, 42.3%; H, 8.6%; N, 16.5%; P, 9.1%; Found: C, 41.9%; H, 8.0%; N, 16.2%; P, 9.2%;

EXAMPLE 7

Ethyl
N-[O-(β-cyanoethyl)-phosphonomethyl]-aminoacetate

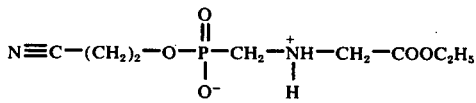

A mixture of 303.3 g (1 mol) of ethyl n-[O-(β-cyanoethyl)-phosphonomethyl]-aminoacetate and 600 ml of water is heated under reflux for 1½ hours. After about 1 hour 10 g of charcoal are added to the reaction mixture. After filtration the water is evaporated at 50° in a rotary evaporator under reduced pressure from a water pump and the residue is treated with boiling ethanol. Colorless crystals, m.p. 198°, are obtained as a product.

Analysis: $C_8H_{15}N_2O_5P$ Molecular weight: 250.19

Calc.: C, 38.4%; H, 6.0%; N, 11.2%; P, 12.3%; Found: C, 38.8%; H, 6.3%; N, 11.1%; P, 12.3%;

Instead of using the indicated starting material as a pure compound in this process, the reaction mixture from the process described in Example 11 following can be used in the hydrolysis reaction.

EXAMPLE 8

Sodium salt of ethyl
N-[O-(β-cyanoethyl)-phosphonomethyl]-aminoacetate dihydrate

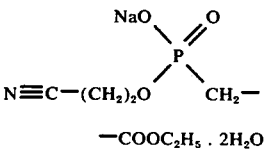

To a solution of 5.00 g (0.02 mol) of ethyl N-[O-(β-cyanoethyl)-phosphonomethyl]-aminoacetate in 100 ml of water are added 20 ml (0.02 ml) of 1N sodium hydroxide with stirring. After evaporation of the water at 50° in a rotary evaporator under reduced pressure from a water pump, the product remains as a syrup.

Analysis: $C_8H_{14}N_2O_5PNa \cdot 2H_2O$ Molecular weight: 308.20

Calc.: C, 31.2%; H, 5.9%; N, 9.1%; P, 10.5%; Found: C, 31.6%; H, 5.7%; N, 9.3%; P, 10.6%;

NMR (δ, ppm) in $D_2O$; protons of —$CH_2$— adjacent to the P atom appear as a doublet at 2.88; those of —$CH_2$— adjacent to the carboxylate group appear as a singlet at 3.56.

EXAMPLE 9

Mono-isopropylammonium salt of ethyl N-[O-(β-cyanoethyl)-phosphonomethyl]-aminoacetate hemihydrate

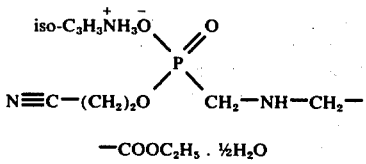

—$COOC_2H_5 \cdot \frac{1}{2}H_2O$

This compound is produced in an analogous manner to that described in Example 8. The product is a syrupy substance.

Analysis: $C_{11}H_{24}N_3O_5P \cdot 1/2H_2O$ Molecular weight: 318.36

Calc.: C, 41.5%; H, 7.7%; N, 13.2%; P, 9.7%; Found: C, 41.8%; H, 7.8%; N, 12.9%; P, 9.5%;

NMR (δ, ppm) in $D_2O$; protons of —$CH_2$— adjacent to the P atom appear as a doublet at 2.90; those of —$CH_2$— adjacent to the carboxylate group appear as a singlet at 3.6.

EXAMPLE 10

Di-methylammonium salt of ethyl N-[O-(β-cyanoethyl)-phosphonomethyl]-aminoacetate dihydrate

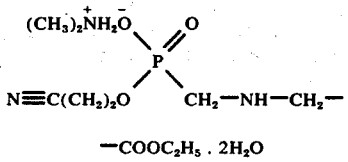

—$COOC_2H_5 \cdot 2H_2O$

This compound is produced in an analogous manner to that described in Example 8. The product is a syrupy substance.

Analysis: $C_{10}H_{22}N_3O_5P \cdot 2H_2O$ Molecular weight: 331.31

Calc.: C, 36.3%; H, 7.9%; N, 12.7%; P, 9.3%; Found: C, 36.7%; H, 7.5%; N, 12.7%; P, 8.9%;

NMR (δ, ppm) in $D_2O$: protons of —$CH_2$— adjacent to the P atom appear as a doublet at 2.90; those of —$CH_2$— adjacent to the carboxylate group appear as a singlet at 3.64.

The starting material of general formula II can be produced as exemplified in the following example.

EXAMPLE 11

Ethyl N-[O,O-Di(β-cyanoethyl)-phosphonomethyl]-aminoacetate

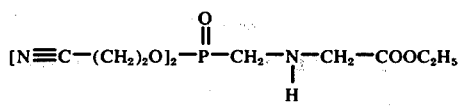

A mixture of 188.1 g (1 mol) of di-(β-cyanoethyl)-phosphite and 115.1 g (0.033 mol) of 1,3,5-tri-(ethoxycarbonylmethyl)-hexahydro-1,3,5-triazine (a trimer of the Schiff's base from formaldehyde and ethyl aminoacetate) is stirred at 100° for ½ hour during which a exothermic reaction is initiated. The reaction mixture can be separated by passage through a silica gel column using n-hexane:acetone (1:1 to 1:3) as the eluant. Thereby a pure product as an oil, $n_D^{20}$ = 1.473, is obtained.

Analysis: $C_{11}H_{18}N_3O_5P$ Molecular weight: 303.26

Calc.: C, 43.6%; H, 6.0%; N, 13.9%; P, 9.2%; Found: C, 43.4%; H, 6.1%; N, 13.3%; P, 9.6%;

NMR (δ, ppm) in $CDCl_3$: protons of —$CH_2$— adjacent to the P atom appear as a doublet at 3.21; those of —$CH_2$— adjacent to the carboxylate group appear as a singlet at 3.53.

The starting material of general formula III can be produced as exemplified in the following example.

EXAMPLE 12

Di-(β-cyanoethyl)-phosphite

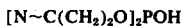

To a suspension of 241.2 g (1 mol) of tri-(β-cyanoethyl)-phosphite in 40 ml of diethyl ether are added with stirring 26 g (1.44 mol) of water. The mixture is refluxed with vigorous stirring during 1½ hours.

The cooled mixture is decanted, and the ethereal phase is discarded and the aqueous phase is evaporated to dryness in vacuo in a rotary evaporator. To the residue is added chloroform and the resulting solution is dried over anhydrous magnesium sulphate, evaporated at 50° in a rotary evaporator under reduced pressure from a water pump, and the residue is then warmed at 80° for ½ hour, followed by 110° for a further ½ hour.

After chromatography the product is obtained as a relatively stable, yellow syrup, $n_D^{20}$ of 1.462.

The purity can be investigated through thin layer chromatography on silica gel with n-hexane:acetone (1:2) as the eluant. Thereby a Rf value is found to be 0.35.

The reaction can be repeated using in the above procedure tri(β-cyanoethyl)-phosphite as the crude product as obtained from the procedure described in Example 13.

EXAMPLE 13

Tri-(β-cyanoethyl)-phosphite

To a mixture of 137.3 g (1 mol) of phosphorous trichloride in 400 ml of absolute benzene is added with stirring 320 g (3.16 mol) of triethylamine in 1400 ml of benzene. The resulting mixture is cooled to 5° and 224 g (3.16 mol) of β-cyanoethanol are added dropwise at this temperature during 1 hour. After being left to stand at 20° for a further 2 hours the precipitated triethylamine hydrochloride is removed by filtration and washed with benzene. The benzene filtrate is evaporated and a residual syrup is obtained. This can be used without purification for further reactions.

After being dried at 80° under high vacuum the nondistilled practically pure product has a refractive index, $n_D^{20}$ of 1.472.

EXAMPLE 14

1,3,5-Tri-(ethoxycarbonylmethyl)-hexahydro-1,3,5-triazine

To 139.6 g (1 mol) of ethyl glycinate hydrochloride are added with stirring 100 g of 36% aqueous formaldehyde solution (1.2 mol). On mixing, an endothermic reaction ensues. Thereafter the mixture is cooled to 10° and 100 ml of a 30% sodium hydroxide solution are added during 1 hour. The mixture is stirred at 20° for a further ½ hour and extracted with 300 ml of chloroform. The chloroform solution is dried over anhydrous magnesium sulphate, evaporated at 50° to dryness under reduced pressure from a water pump and dried at 50° under high vacuum. The product obtained is a colorless oil. It is pure as indicated by thin layer chromatography and can be used for further reaction without purification. It has a refractive index, $n_D^{20}$ of 1.478.

I claim:

1. A compound of the formula

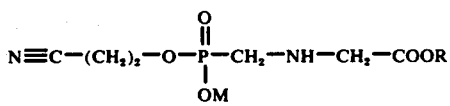

wherein

R is hydrogen, a hydrocarbon ($C_1$–$C_{12}$) unsubstituted or substituted by halogen, alkoxy ($C_1$–$C_8$), di-alkyl ($C_1$–$C_8$) amino or cyano, or an agriculturally acceptable cation and, M is hydrogen or an agriculturally acceptable cation.

2. A compound of claim 1 of the formula

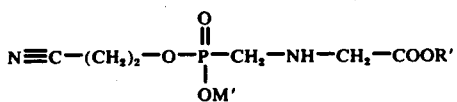

wherein

R' is hydrogen, alkyl ($C_1$–$C_5$) or a sodium or potassium cation or a cation of formula (b)

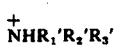   b wherein $R_1'$, $R_2'$, and $R_3'$ are each, independently, hydrogen or alkyl ($C_1$–$C_4$), and M' is hydrogen or a sodium or potassium cation or a cation of formula (b) as defined above.

3. The compound of claim 1 which is N-[O-(β-cyanoethyl)-phosphonomethyl]-glycine.

4. The compound of claim 1 which is N-[O-(β-cyanoethyl)-phosphonomethyl]-glycine hydrate in monosodium salt form.

5. The compound of claim 1 which is N-[O-(β-cyanoethyl)-phosphonomethyl]-glycine hydrate in monoisopropylammonium salt form.

6. The compound of claim 1 which is N-[O-(β-cyanoethyl)-phosphonomethyl]-glycine dihydrate in dimethylammonium salt form.

7. The compound of claim 1 which is N-[O-(β-cyanoethyl)-phosphonomethyl]-glycine hydrate in disodium salt form.

8. The compound of claim 1 which is N-[O-(β-cyanoethyl)-phosphonomethyl]-glycine hydrate in diisopropylammonium salt form.

9. The compound of claim 1 which is ethyl N-[O-(β-cyanoethyl)-phosphonomethyl]-aminoacetate.

10. The compound of claim 1 which is ethyl N-[O-(β-cyanoethyl)-phosphonomethyl]-aminoacetate dihydrate in sodium salt form.

11. The compound of claim 1 which is ethyl N-[O-(β-cyanoethyl)-phosphonomethyl]-aminoacetate hemihydrate in mono-isopropylammonium salt form.

12. The compound of claim 1 which is ethyl N-[O-(β-cyanoethyl)-phosphonomethyl]-aminoacetate dihydrate in dimethylammonium salt form.

13. A herbicidal or plant growth regulator composition comprising a herbicidally or plant growth regulating effective amount of a compound of claim 1 in association with a herbicide or plant growth regulator carrier, diluent and/or adjuvant.

14. A method of combating weeds in a locus which comprises applying to said locus a herbicidally effective amount of a compound of claim 1.

15. A method of combating weeds in a cultivated crop locus which comprises applying to said locus a herbicidally selective amount of a compound of claim 1.

16. A method of regulating the growth of cultivated plants which comprises applying to said plants a plant growth regulating amount of a compound of claim 1.

17. A method according to claim 16, wherein said cultivated plants comprise cucumbers, beans, fruit crops, tobacco, hemp or cotton.

* * * * *